United States Patent [19]

Kensey et al.

[11] Patent Number: 5,170,805
[45] Date of Patent: Dec. 15, 1992

[54] METHOD OF DESTROYING TISSUE SUCH AS A GALL BLADDER UTILIZING A SCLEROSING AGENT ALONE OR WITH A SYMPHYSIS AGENT

[75] Inventors: Kenneth Kensey, Chester Springs; John Nash, Downingtown, both of Pa.

[73] Assignee: Kensey Nash Corporation, Exton, Pa.

[21] Appl. No.: 626,073

[22] Filed: Dec. 11, 1990

[51] Int. Cl.$^5$ .............................................. A61B 19/00
[52] U.S. Cl. ..................................... 128/898; 606/128; 606/159; 604/22; 604/82
[58] Field of Search ................. 606/46, 135, 159, 128; 128/898; 604/22, 28, 82, 903

[56] References Cited

U.S. PATENT DOCUMENTS

| | | | |
|---|---|---|---|
| 3,316,910 | 5/1967 | Davis | 606/128 X |
| 3,942,519 | 3/1976 | Shock | 606/128 X |
| 4,601,698 | 7/1986 | Moulding, Jr. | 604/22 X |
| 4,857,046 | 8/1989 | Stevens et al. | 606/159 X |
| 4,902,276 | 2/1990 | Zakko | 604/28 |
| 5,018,508 | 5/1991 | Fry et al. | 604/28 X |
| 5,037,431 | 8/1991 | Summers et al. | 604/22 X |

*Primary Examiner*—Peter A. Aschenbrenner
*Attorney, Agent, or Firm*—Ceasar, Rivise, Bernstein, Cohen & Pokotilow, Ltd.

[57] ABSTRACT

A method of destroying tissue such as a gall bladder located within the body of a living. A sclerosing agent is introduced into the body in a volume contiguous with the surface of the tissue to be destroyed. The sclerosing agent comprises a flowable material made up of a liquid carrier and a large plurality of abrasive particles, e.g., acicular particles of carborundum, silicon carbide, etc., Optionally, a symphysis agent, such as an antibiotic, may be introduced into the volume. Once the agent is introduced, it is caused to circulate therein whereupon its scrapes across the surface of the tissue to effect the sclerosing thereof.

41 Claims, 1 Drawing Sheet

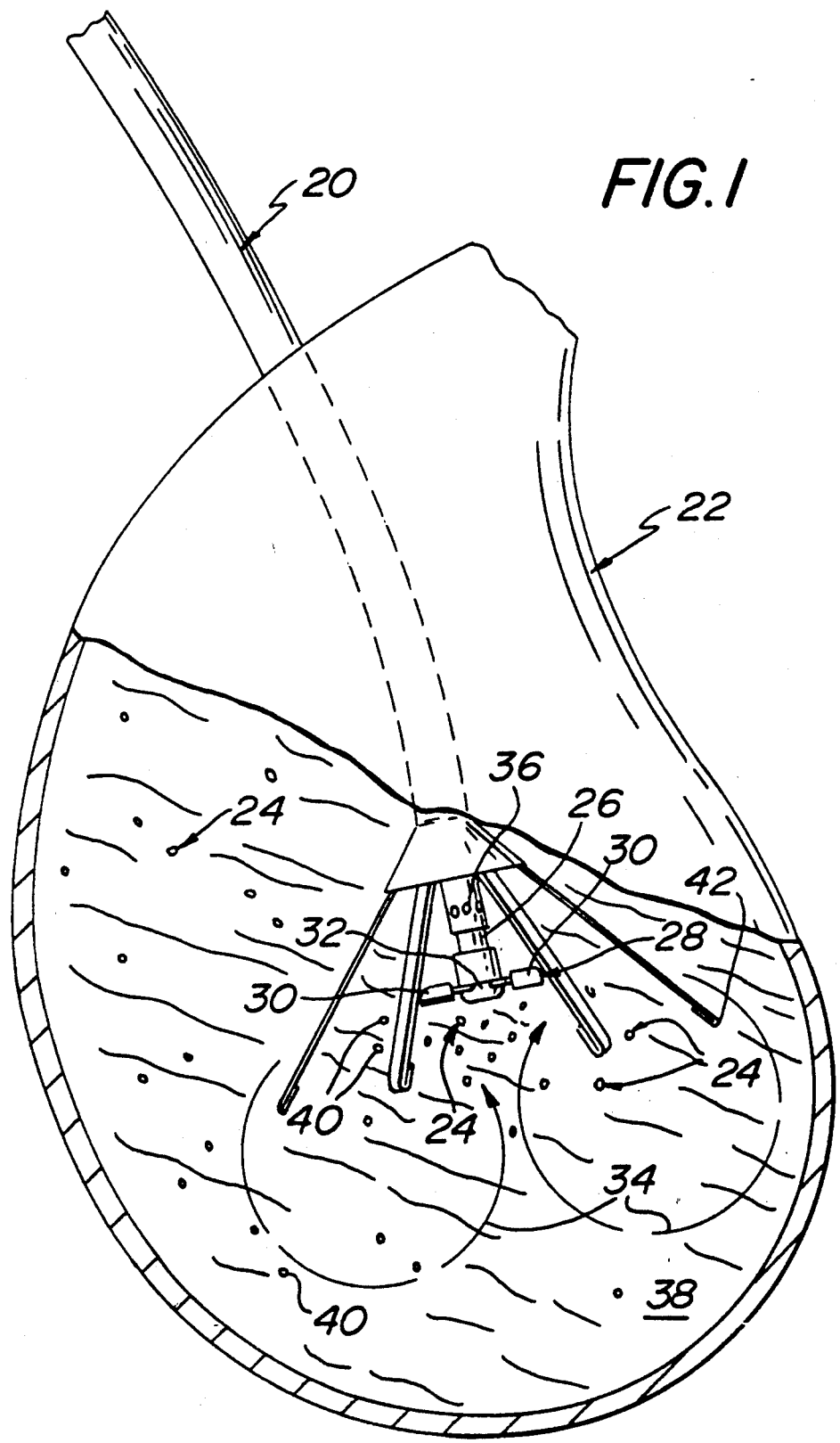

METHOD OF DESTROYING TISSUE SUCH AS A GALL BLADDER UTILIZING A SCLEROSING AGENT ALONE OR WITH A SYMPHYSIS AGENT

BACKGROUND OF THE INVENTION

This invention relates generally to methods of performing non-invasive medical procedures on a living being, and more particularly to a method for expeditiously destroying tissue, such as a gall bladder, located within a living being by circulating a sclerosing agent therein/thereabout. In addition, the method may also comprise the step of introducing a symphysis agent before, simultaneously or after the introduction of the sclerosing agent.

Medical instruments, such as catheters having working heads located at the free end thereof, are widely accepted in the medical community for effecting various procedures within a patient which had previously been accomplished by general surgery. Those instruments have thus opened the way for what has become known as "non-invasive" surgery. The destruction of stones, e.g., gallstones, kidney stones, etc. is one area in which non-invasive procedures are undergoing significant evolution, and several patents and patent applications are directed thereto.

For example, in U.S. Pat. No. 4,679,558 (Nash et al.), assigned to the same assignee of this invention there is disclosed and claimed an instrument for effecting the destruction of a stone or other hard body located within the body of a living being. That instrument basically comprises a catheter having a working head located at its distal end. The working head is arranged to engage the stone to mechanically destroy, e.g., pulverize, it.

In U.S. Pat. No. 4,811,735 (Nash et al.), also assigned to the same assignee of this invention and whose disclosure is incorporated by reference herein there is disclosed and claimed an improved catheter and method of use for disintegrating or otherwise destroying a stone, such as a gallstone, within the body of a living being. That catheter basically comprises a small diameter instrument with a working head located at the distal end thereof. The catheter is capable of being located at any position within the patient's body so that the working head is located adjacent the stone to be destroyed. The working head comprises a bladed member having at least one impacting surface thereon. In accordance with one aspect of that invention, the bladed member is arranged to be moved from a retracted position, wherein its impacting surface is located adjacent the periphery of the catheter, to an extended position, wherein the impacting surface extends substantially beyond the periphery of the catheter. The working head is arranged to be rotated at a high speed about the longitudinal axis of the catheter when the impacting surface is extended. Thus, the impacting surface repeatedly impacts the stone to disintegrate or otherwise destroy it. The rotation of the working head serves to create a vortex flow in the liquid which is located at the situs of the stone. This vortex flow tends to pull the stone into the rotating impacting surface(s) to expedite the destruction of the stone. A shroud is provided about the distal end of the catheter to aid in directing the stone to the rotating blade while also protecting adjacent body tissue from being engaged by the rotating blade.

In U.S. patent application Ser. No. 07/322,754 filed on Mar. 13, 1989, entitled Stone Pulverizing Apparatus With Improved Working Head And Method Of Use, which is assigned to the same assignee as this invention and whose disclosure is incorporated by reference herein, there is disclosed yet a further improvement in a stone destroying instrument, e.g., catheter, and its method of use. In accordance with on aspect of that invention the catheter utilizes a working head comprising at least two radially extending, blade-like members. Each blade-like member includes plural force-concentrating impacting surfaces and interposed grooves. The working head is arranged to be rotated at a high speed about the longitudinal axis of the catheter so that the impacting surfaces repeatedly engage the stone. The rotation of the working head produces a flow of the liquid in which the stone is located past the working head, with some portion of the liquid flowing through the plural grooves. The fluid flowing through the grooves reduces any boundary layer effect which would tend to sweep smaller particles away from the impacting surfaces. Accordingly, the efficient pulverization of the particles and the destruction of the stone is effected without appreciable injury to the body of the being.

In U.S. application Ser. No. 07/395,248 filed on Aug. 17, 1989, assigned to the same assignee as the present invention, is disclosed a method of mechanically destroying stones in a living being using vortex flow in a viscous fluid. The viscous liquid containing the stones helps to carry the stones into a position where they can be readily pulverized or otherwise destroyed and also tends to increase the vortex flow created by rotation of the working head of the stone destroying instrument.

All of these instruments disclosed in the aforementioned patents and patent applications are introduced into the portion of the patient's body, e.g., the gall bladder, where the stone(s) to be destroyed is (are) located. Saline solution is typically introduced into that body portion, and as the stone destruction process is carried out, i.e., as the stones are pulverized, the saline solution and stone particles produced by the process are extracted and fresh saline introduced.

After the destruction of the stones has been accomplished it is oftentimes necessary and/or desirable to also destroy or otherwise remove the gall bladder itself to prevent the reoccurrence of stones. Moreover, in some instances the removal of the gall bladder, without first removing or destroying any stones which may exist, is desirable. While this can be accomplished by general surgical procedures, it is desirable to be able to destroy the gall bladder by less intrusive procedures.

To that end in U.S. patent application Ser. No. 07/380,930, filed on Jul. 14, 1989, entitled Apparatus and Method For Sclerosis of Body Tissue, which is assigned to the same assignee as this invention, there is disclosed and claimed a an instrument for mechanically sclerosing the inner surface of the gall bladder so that the gall bladder undergoes necrosis and is ultimately absorbed by the patient's body.

The instrument disclosed and claimed in that application basically comprises a small diameter, elongated, flexible catheter having a longitudinal central axis and a movable working head located at the distal end thereof. The working head comprises a flexible member having a free end portion arranged to be extended generally outward radially from a retracted radial position with respect thereto when the apparatus is located within a body organ, and means for rotating the working head at a high rate of speed whereupon the free end portion engages tissue forming the organ's inner surface to mechanically denude the tissue.

In addition, to the foregoing prior art, the medical literature discloses the use of liquids to sclerose or ablate certain body portions or tissues of the body. One such use not involving gall bladders includes the intrapleural administration of bleomycin to serve as an effective sclerosing agent. R. D. Siegel, et al., Systemic Toxicity Following Intracavitary Administration of Bleomycin, *Chest* 1990 Aug.; 98(2):507. However, this study also concludes that this treatment may cause complications and/or serious side effects with patients having renal dysfunction.

Sclerotherapy using tetracycline has also been utilized in the treatment of hydroceles and epididymal cysts apparently with short term effectiveness and a long term cure rate of 77%. M. Honnens de Lichtenberg, et al., Tetracycline Sclerotherapy Of Hydroceles and Epididymal Cysts, *Acta. Chir. Scand.* 1990 Jun.-Jul.; 156(6-7); 439-40. Sclerotherapy is also reported to be suitable for outpatient therapy for the treatment of hydroceles utilizing a 3% sodium tetradecyl sulfate and 3.5% rolitetracycline solution. R. K. Rencken, et al., Sclerotherapy for hydroceles, *J. Urol.* 1990 May; 143(5):940-3.

Sclerotherapy has also been utilized in the prophylactic administration of antibiotics such as intravenous ampicillin in the sclerotherapy of esophageal varices. R. Pulanic, et al., Controlled Trial of the Prophylactic Administration of Antibiotics in Sclerotherapy of Esophageal Varices, *J. Chemother.* 1989 Aug.; 1(4);261-5.

While scientists have investigated various types of solutions in sclerotherapy, tetracycline has been widely experimented with since it is easy to administer, is readily available at a relatively low cost and has a low morbidity rate. In this regard, medical personnel have attempted to utilize tetracycline in the sclerotherapeutic treatment of various cancers. A. Contegiacomo, et al., The Treatment of Metastatic Pleural Effusion in Breast Cancer, *Tumori* 1987 Dec. 81;73(6);611-6; A. W. Lees, W. Hoy, Management of Pleural Effusions in Breast Cancer, *Chest* 1979 Jan.;75(1):51-3; T. C. Bayly, et al., Tetracycline and Quinacrine in the Control of Malignant Pleural Effusions, *Cancer* 1978 Mar.;41(3):1188-92.

Although the use of sclerosing agents has been widely experimented with, the rate of success in producing tissue symphysis is quite variable depending upon such factors as solution pH, etc. S. A. Sahn, et al., The pH of Sclerosing Agents: A Determinant of Pleural Symphysis, *Chest* 1979 Aug.;76(2):198-200.

It has been suggested by Dr. Christoph D. Becker, et al., Department of Radiology, University of Bern, Inselspital, Bern, Switzerland, *Radiology* April 1989; 171:235-240, to effect the destruction of the gall bladder in pigs by electrocoagulation of the cystic duct, followed by the introduction of ethanol and sodium tetradecyl-sulfate, to chemically sclerose the gall bladder inner surface whereupon the gall bladder eventually undergoes necrosis and absorption. This procedure however, has been criticized for use in humans, as being non-compatible with and/or ineffective for the human system. Dr. Robert C. Hall, *Radiology* Nov. 1989; 578-580. Dr. Becker has also utilized the procedure on humans with mixed results, including problems associated with mucosal regeneration. Dr. Christoph D. Becker, et al., *Radiology* Sep. 1990; 687-690.

While the use of alcohol as a sclerosing agent for the gall bladder may be generally sufficient to ultimately effect its destruction, it appears to leave something to be desired from the standpoint of efficiency and/or speed and/or effectiveness of the sclerosing action.

A need thus exists for a method for destroying tissue such as a gall bladder, utilizing a sclerosing agent and/or a symphysis agent which permits the body to absorb the destroyed gall bladder after treatment thereof.

OBJECTS OF THE INVENTION

Accordingly, it is a general object of this invention to provide a method of sclerosing tissue, e.g., the gall bladder, within the body of a living being, which method overcomes the disadvantages of the prior art.

It is a further object of this invention to provide a method of sclerosing the gall bladder of a living being to effect its destruction in a safe, effective and expeditious manner, while minimizing trauma.

It is a further object of this invention to provide a method of mechanically sclerosing tissue, e.g., the gall bladder, within the body of a living being and for effecting symphysis of the sclerosed tissue.

It is yet another object of this invention to provide a method of destroying a gall bladder which permits the body to absorb the organ after treatment thereof.

SUMMARY OF THE INVENTION

These and other objects of this invention are achieved by providing a method of destroying tissue located within the body of a living, e.g., a gall bladder, the tissue being located adjacent a volume into which a flowable material may be introduced and having a surface contiguous with the volume. The method comprises introducing a flowable material comprising a liquid carrier and a large plurality of abrasive particles into the volume, creating a circulating flow of the flowable material within the volume, whereupon the flowable material engages the surface of the tissue to effect the sclerosing thereof.

BRIEF DESCRIPTION OF THE DRAWING

Other objects and many attendant advantages of this invention will become readily appreciated as the same becomes better understood by reference to the following detailed description when considered in connection with the accompanying drawing, identified as FIG. 1, which is a schematic diagram showing a typical apparatus for carrying out the ablation of a gall bladder in accordance with the teachings of this invention.

DETAILED DESCRIPTION OF THE PREFERRED EMBODIMENT

Referring now in greater detail to the figures there is shown at 20 in FIG. 1, an instrument which is preferably in accordance with the teachings of the aforenoted patents and patent applications, shown located within the gall bladder 22 of a living being to be operated in accordance with the method of this invention.

As will be described later the instrument 20 is arranged to introduce a flowable sclerosing agent into the interior of the gall bladder. Preferably the sclerosing agent comprises a liquid carrier having a large number of abrasive particles therein. The sclerosing agent is caused to flow across the interior surface of the gall bladder so that the tissue is abraded sufficiently that it will atrophy, whereupon the gall bladder will eventually be absorbed by the body.

It must be pointed out at this juncture that the specific instrument 20 used, is merely exemplary. Thus, in accordance with the teachings of this invention, and as adapted for various conditions of service, any instrument apparatus which can create a flow of material within/about the tissue to be destroyed may be used. In addition, it should be readily apparent to those skilled in the art that the instant invention may be utilized to destroy various types of body tissue, and is not limited to merely the destruction of gall bladder tissue.

The instrument 20 basically comprises a small diameter, elongated, catheter having a distal end 26 at which a working head 28 is located. In the device 20 shown in the drawing, the working head 28 is a bladed member which is arranged to be rotated at a high rate of speed about the longitudinal axis of the device. This action produces a circulating or vortex flow in the liquid within the gall bladder as described in further detail below.

In the preferred embodiment, the catheter is flexible to permit manipulation into the entrance of the cystic duct of the gall bladder 22, for example. However, any suitable small diameter instrument, flexible or rigid, may be utilized.

The working head of the catheter includes a pair of blades 30 mounted on a central hub 32. The hub 32 is arranged to be rotated at a high rate of speed about the central longitudinal axis of the catheter by a proximally located motor (not shown) via a drive member (not shown) extending down the interior of the catheter.

The blades may be of a fixed size or may be extendable. In the latter case the blades are mounted on the hub so that they are normally in a retracted position located adjacent the central longitudinal axis of the catheter. However, as the working head rotates, the centrifugal force on the blades causes the blades 30 to pivot outward from the retracted position to a radially extended position, whereupon the blades are located approximately perpendicularly to the axis of rotation of the working head.

If the apparatus uses blades of a fixed size they are mounted so they always extend outward, generally radially from the central longitudinal axis of the device. Whether the blades are fixedly mounted or extendable, they are oriented so that they are at a slight helix angle to the longitudinal axis of the catheter so that when they ar rotated they create a vortex flow in the liquid within the gall bladder 22.

In the embodiment shown herein the vortex flow is in the direction of arrows 34. This is merely exemplary and the flow could be in the opposite direction so long as it causes the liquid in the gall bladder to sweep across the tissue forming the inner surface of the gall bladder.

The distal end of the catheter adjacent the working head 28 includes plural apertures 36 which are in fluid communication with the interior of the catheter. These apertures provide the means of introducing and removing the sclerosing agent into the gall bladder. That agent basically comprises a liquid carrier 38 and a large plurality of abrasive particles 24 (only a few of which are shown in the interest of drawing simplicity) to aid in the destruction of the gall bladder 22. As will be described later, the agent may also include a fusing liquid.

In order to protect the surrounding tissue from being damaged by the rotating blades, if this is a concern, the distal end of the catheter may include a shroud assembly in the form of an expansible basket 42 located thereat. When the basket 42 is expanded over the catheter's blades 30, the blades are prevented from engaging the tissue walls 40 of the gall bladder 22.

The flow of the liquid within the gall bladder is, as noted earlier, preferably a vortex flow or other circulating flow. That flow can be created by the rotating blades 30 or any other suitable means. In any event, the liquid carrier 38 and the particles 24 therein are preferably recirculated within the gall bladder to cause the particles to scrape against the interior surface 40 of the gall bladder.

The vortex 34 is made more powerful by utilizing a liquid carrier 38 having a viscosity greater than water, and preferentially in the range of about 1 to 200 centipoise at 70 degrees Fahrenheit. As an example, a liquid (or any mixture thereof) such as ethanol, saline or a contrast media such as RENOGRAFIN 76, a radio-opaque fluid used in angiography, comprising diatrizoate meglumine and diatrizoate sodium, sold by Squibb Diagnostics may be used.

The increased vortex flow occurs in use with liquid carriers having the desired viscosity because the impeller function of the rotating blades 30 partially acts as an axial flow pump and largely as part of a spinning disc which can pump radially due to friction drag. This radial pumping component increases as the liquid viscosity increases.

Since this invention is not limited to circulating the abrasive particles 24 in only a vortex flow pathway, any means and/or method to introduce or inject the abrasive particles 24 and to move those particles across the inner surface of the gall bladder so as to effectively sclerose the desired tissue may be used.

The abrasive particles 24 may be comprised of almost any suitable material. Preferably the particles 24 have sharp angles, e.g., are acicular, to expedite in the abrasive action of the sclerosing agent. Moreover, in the preferred method of this invention, the abrasive particles 24 are chosen among the group of carborundum, silicon carbide, aluminum oxide, silica, etc., and are in the range of from 5 microns to one mm in diameter.

After sufficient tissue abrasion (sclerosis) of the interior surface 40 of the gall bladder 22 or other tissue has occurred, the liquid carrier 38 and abrasive particles 24 may be withdrawn through the plural apertures 36 or via some other means (not shown).

In an alternative method of the invention, the method additionally comprises introducing a fusing liquid or chemical into the gall bladder 22, which causes symphysis (fusing) of the interior walls of the gall bladder to facilitate gall bladder atrophication. This fusing liquid may be introduced either after, simultaneously or before the circulation of the abrasive particles 24, depending upon the circumstances of use.

Although any suitable fusing liquid or chemical may be utilized for this purpose, such as nitrogen mustard or quinacrine, it is preferable that the fusing liquid comprise an antibiotic. Although any suitable antibiotic may be utilized, it is preferable that the antibiotic be chosen from the group of ampicillin, bleomycin, ampicillin, rolitetracycline (preferably added in the presence of sodium tetradecyl sulfate) and tetracycline. Tetracycline is the preferred antibiotic fusing liquid of the present invention as it is easy to obtain, is low in cost, is simple to administer, and is less toxic than other fusing liquids.

After treatment of the gall bladder and removal of the catheter or other instrument used to effect the desired action, the gall bladder interior 40 will be traumatized sufficiently to accelerate the atrophication thereof. In addition, if a fusing liquid is utilized, the interior walls of the gall bladder will also undergo symphysis to further accelerate gall bladder atrophication. The gall bladder will stop functioning and necrosis will occur whereupon it will be effectively absorbed by the body.

Without further elaboration the foregoing will so fully illustrate our invention that others may, by applying current or future knowledge, adopt the same for use under various conditions of service.

We claim:

1. A method of destroying tissue located within the body of a living being, said tissue being located adjacent a volume into which a flowable material may be introduced, said tissue having a surface contiguous with said volume, said method comprising introducing a flowable material comprising a liquid carrier and a large plurality of abrasive particles into said volume, creating a circulating flow of said material within said volume whereupon said flowable material engages said surface of said tissue to effect the sclerosing thereof.

2. The method of claim 1 wherein said liquid has a viscosity of at least 1 at 70 degrees Fahrenheit.

3. The method of claim 1 wherein said particles are acicular.

4. The method of claim 2 wherein said particles are acicular.

5. The method of claim 1 wherein said particles are of a size in the range of 5 microns to 1 mm in diameter.

6. The method of claim 2 wherein said particles are of a size in the range of 5 microns to 1 mm in diameter.

7. The method of claim 3 wherein said particles are of a size in the range of 5 microns to 1 mm in diameter.

8. The method of claim 5 wherein said particles are of a size in the range of 5 microns to 1 mm in diameter.

9. The method of claim 2 wherein said liquid has a viscosity in the range of 1 to 100 centipoise at 70 degrees Fahrenheit.

10. The method of claim 3 wherein said liquid has a viscosity in the range of 1 to 100 centipoise at 70 degrees Fahrenheit.

11. The method of claim 5 wherein said liquid has a viscosity in the range of 1 to 100 centipoise at 70 degrees Fahrenheit.

12. The method of claim 1 wherein said tissue is the gall bladder.

13. The method of claim 12 wherein said liquid has a viscosity of at least 1 centipoise at 70 degrees Fahrenheit.

14. The method of claim 12 wherein said particles are acicular.

15. The method of claim 13 wherein said particles are acicular.

16. The method of claim 1 wherein the liquid is selected from the group of ethanol, saline or a contrast media.

17. The method of claim 2 wherein the liquid is selected from the group of ethanol, saline or a contrast media.

18. The method of claim 3 wherein the liquid is selected from the group of ethanol, saline or a contrast media.

19. The method of claim 1 wherein the abrasive particles are chosen from the group of carborundum, silicon carbide, aluminum oxide and silica.

20. The method of claim 2 wherein the abrasive particles are chosen from the group of carborundum, silicon carbide, aluminum oxide and silica.

21. The method of claim 3 wherein the abrasive particles are chosen from the group of carborundum, silicon carbide, aluminum oxide and silica.

22. The method of claim 1 additionally comprising the step of introducing a fusing liquid into said volume and permitting said fusing liquid to remain therein for a predetermined period of time.

23. The method of claim 12 additionally comprising the step of introducing a fusing liquid into said gall bladder and permitting said fusing liquid to remain therein for a predetermined period of time.

24. The method of claim 22 wherein the fusing liquid comprises an antibiotic.

25. The method of claim 23 wherein the fusing liquid comprises an antibiotic.

26. The method of claim 24 wherein the antibiotic is chosen from the group of bleomycin, ampicillin, rolitetracycline and tetracycline.

27. The method of claim 26 wherein the rolitetracycline is introduced in combination with sodium tetradecyl sulfate.

28. The method of claim 11 wherein the concentration of rolitetracycline is approximately 3.5% and the concentration of sodium tetradecyl sulfate is approximately 3%.

29. The method of claim 25 wherein the antibiotic is chosen from the group of bleomycin, ampicillin, rolitetracycline and tetracycline.

30. The method of claim 29 wherein the rolitetracycline is introduced in combination with sodium tetradecyl sulfate.

31. The method of claim 30 wherein the concentration of rolitetracycline is approximately 3.5% and the concentration of sodium tetradecyl sulfate is approximately 3%.

32. The method of claim 22 wherein the fusing liquid comprises nitrogen mustard.

33. The method of claim 23 wherein the fusing liquid comprises quinacrine.

34. The method of claim 1 wherein the circulating flow is a vortex flow.

35. The method of claim 12 wherein the circulating flow is a vortex flow.

36. The method of claim 34 additionally comprising providing a device to be introduced into said volume, wherein the vortex flow is created by the device introduced into said volume and wherein said flowable material is introduced by said device.

37. The method of claim 35 additionally comprising providing a device to be introduced into said volume, wherein the vortex flow is created by the device introduced into said volume and wherein said flowable material is introduced by said device.

38. The method of claim 36 wherein the device is a catheter.

39. The method of claim 37 wherein the device is a catheter.

40. The method of claim 38 wherein the catheter has a working head.

41. The method of claim 39 wherein the catheter has a working head.

* * * * *